United States Patent [19]
Sewell, Jr.

[11] Patent Number: 5,141,503
[45] Date of Patent: Aug. 25, 1992

[54] WOUND SUCTION DRAINAGE SYSTEM

[76] Inventor: Frank K. Sewell, Jr., 1413 N. Elm, Henderson, Ky. 42420

[21] Appl. No.: 647,548

[22] Filed: Jan. 29, 1991

[51] Int. Cl.$^5$ .............................................. A61M 1/00
[52] U.S. Cl. ..................................... 604/317; 606/159
[58] Field of Search ............... 604/317, 319, 321, 327, 604/328, 356; 606/159

[56] References Cited

U.S. PATENT DOCUMENTS 4,990,137 2/1991 Graham ................................. 604/73

OTHER PUBLICATIONS

Moss, James P.; Historical and Current Perspectives on Surgical Drainage; Surgery, Gynecology & Obstetrics; 1981; 152:517-525.
Zacharski, Lee R. et al.; Mechanism of Obstruction of Closed-Wound Suction Tubing; Archives of Surgery, 1979; 144:614-615.
Lesser, Arthur J.; The Place of Wound Drainage in Surgery with Description of a New Drain, Archives of Surgery, 1960:81-870-873.
Freund, H.: Simple Method to Prolong and Improve the Function of Hemovac Drains; American Journal of Surgery, 1975; 129:600.
Jochimsen, Peter R.; Method to Prevent Suction Catheter Drainage Obstruction; Surgery, Gynecology & Obstetrics, 1976; 142:748-749.
Sondack, Vernon K. et al.; Simple, Inexpensive Technique for Clearing Obstructed Closed Suction Drainage Catheters; Surgery, Gynecology & Obstetrics, 1985; 161:595-596.
Halejan, Barry A. et al.; Maintaining Chest Tube Patency; Surgery, Gynecology & Obstetrics, 1987; 142:521.
Wackym, Phillip A., et al; A New Technique to Maintain Closed-Suction Drainage Catheter Function; Archives of Otolaryngolgy and Hand and Neck Surgery, 1987; 113:57-58.
Zimmer; Wound Drainage; brochure on Synder® products; pp. J6, J8-J10, J12.
DePuy; Infection Control Products; brochure on Hemo-Drain R products; p. J-8.
Alexander; Care of the Patient in Surgery; p. 143.

Primary Examiner—Randy Shay
Assistant Examiner—Gina Gualtieri
Attorney, Agent, or Firm—Baker & Daniels

[57] ABSTRACT

Wound drainage system having a wound drainage catheter with an apertured distal end and a closed reservoir system. A plug in the lumen of the distal end substantially engages the lumen. A thread connects the plug to a pulling mechanism external the closed reservoir system for pulling the thread to move the plug toward the suction end of the catheter to sterilely clear the lumen. The plug may have an aperture so that multiple plugs may be positioned in the lumen, with each plug thread passing through the aperture of each upstream plug. Each plug may be separately pulled through the lumen to clear catheter of occluded material.

25 Claims, 3 Drawing Sheets

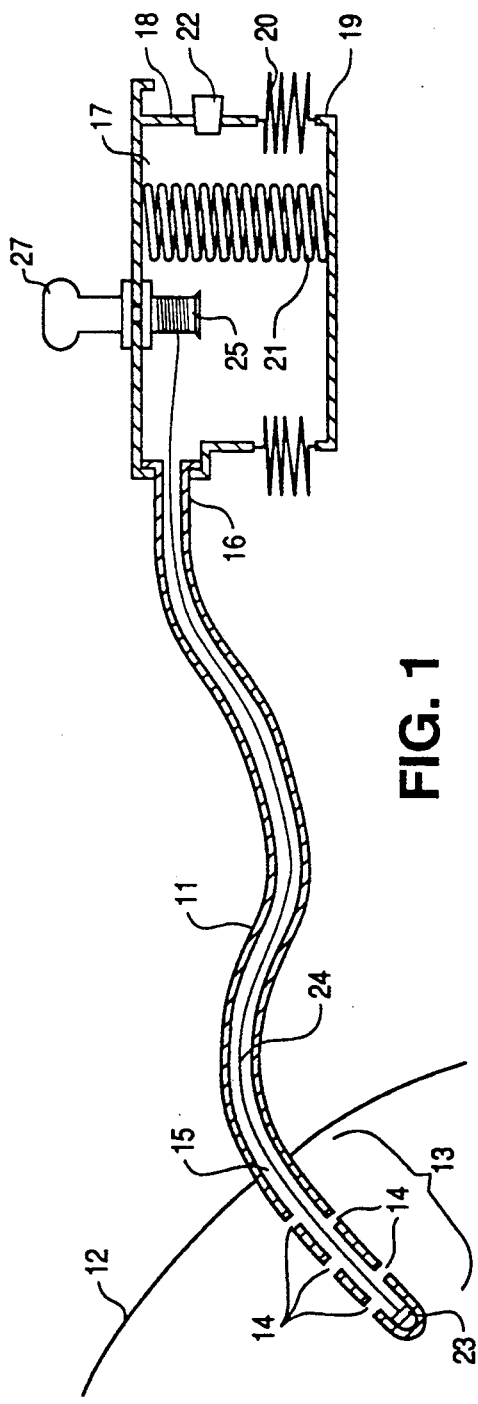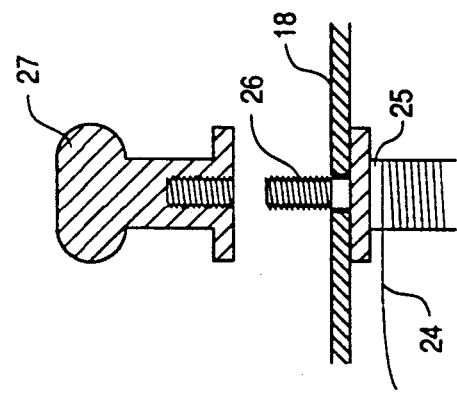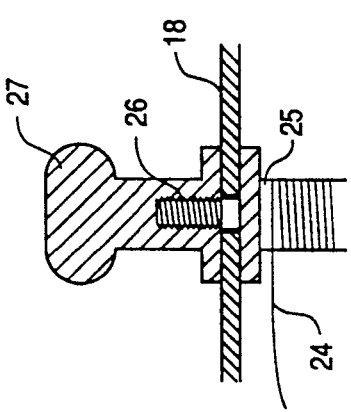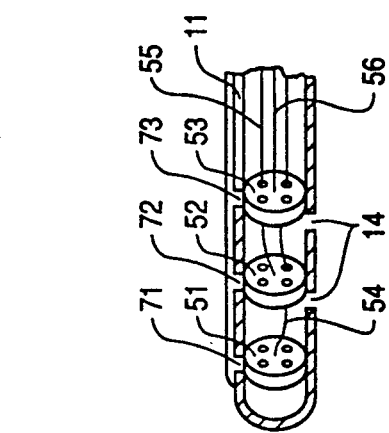
FIG. 1
FIG. 2
FIG. 3
FIG. 4

WOUND SUCTION DRAINAGE SYSTEM

FIELD OF THE INVENTION

The present invention relates to devices for draining fluid from wound sites, including operative wounds.

BACKGROUND OF THE INVENTION

Continuous closed wound suction units which are portable, will not collapse, and are made of a nonreactive material, are used to remove fluids from operative wounds. Many articles have documented the value of closed suction drainage since it was introduced in 1952. One excellent collective review about this subject is Moss, James P., *Historical and Current Perspectives on Surgical Drainage*, Surgery, Gynecology & Obstetrics, 1981; 152: 517-525. The suction catheters are left in place until they are no longer effective, then they are removed. However, the suction catheters may become occluded by tissue, clots, and necrotic material. Although the incidence of this obstruction is low in small wounds, every surgeon has had the experience of removing a suction catheter only to have a gush of serosanguinous fluid come out of the catheter site. A worse experience for the surgeon and patient is to first remove a suction catheter and then have a collection of fluid build up and form an abscess. Obviously, the suction catheter can become obstructed before the fluid in the operative site can be removed.

The mechanism of obstructin has been studied in, for example, Zacharski, Lee R., *Mechanism of Obstruction of Closed-Wound Suction Tubing*, Archives of Surgery, 1979; 144: 644-615. Dr. Zacharski and his associates tested suction catheters for occlusion after they were removed, then cut them into short segments and microscopically examined the contents. Although no occlusion was clinically evident in any one of the twenty-one suction catheters examined, all the tubes were plugged by clots and debris. Some were plugged throughout their entire length, and others showed segmental plugging. Only one out of twenty-one tubes examined was free of any plug. He also noted that solid contents (the plugs) were not adherent to the tube wall. The surprising finding was that organized clots with fibrin were relatively scarce. The plugs were debris and necrotic tissue from muscle, fat, and blood vessels. Accordingly, Dr. Zacharski concluded that meticulous wound flushing should be done at the end of every procedure. This advice was and is followed. Dr. Zacharski also suggested tubes of different designs. Silastic rigid tubes with multiple perforations are now commercially available and appear to work best. However, suction catheter drains still become occluded especially in the patients who have had the more extensive surgical procedures. These are the very patients who cannot afford to develop an occlusion, an abscess, or an infection It is also well known that catheters or drains and the wound around them are a conduit for bacteria, and overwhelming evidence shows this to be a two way conduit. Therefore, surgeons cannot simply use more drains, larger drains, or squirt fluid through the drain back into the patient's wound to remove the debris and clots from a suction drainage catheter. One alternative is disclosed by Arthur J., in *The Place of Wound Drainage in Surgery with Description of a New Drain*, Archives of Surgery, 1960; 81: 870-873, which discloses use of a Foley catheter. A double lumen construction permits aspiration, irrigation with saline, or continuous drip with suction. Freund, H., *Simple Method to Prolong and Improve the Function Hemovac Drains*, American Journal of Surgery, 1975; 129: 600. discloses drainage tubes aspirated with a needle and syringe. Dr. Peter R. Jochinsen in *Method to Prevent Suction Catheter Drainage Obstruction*, Surgery, Gynecology, and Obstetrics, 1976; 142: 748-749, disclosed dividing the drainage tube at the time of surgery, interposing a soft rubber tube, and the stripping the collapsible rubber tube toward the suction catheter every day. Sondak, Vernon K., *A Simple Inexpensive Technique for Clearing Obstructed Closed Suction Drainage Catheters*, Surgery, Gynecology, and Obstetrics, 1985; 161: 595-596, discusses a "catheter thrombectomy. A Fogarty balloon tipped catheter uses a central venous catheter for the "catheter thrombectomy." Halejian, Barry Aud, *Maintaining Chest Tube Patency*, Surgery, Gynecology, and Obstetrics, 1987; 142: 521, discloses a respirator suction catheter for the same purpose. Finally Wackym, Phillip Ashley, *A New Technique to Maintain Closed-Suction Drainage Catheter Function*, Archives of Otolaryngology and Hand and Neck Surgery, 1987, 113: 57-58 discloses a pediatric feeding tube and syringe to clear the suction catheter. incidentally, the article discusses a catheter obstruction incidence of about 3%, but this percentage would vary with diameter of the drain, amount of suction, size of the wound, and a whole host of other variables.

Despite accepted recognition of the desirability of keeping a closed suction closed, the recommendations in the literature about methods to clear the suction catheter of clots and debris violate the closed system concept. Moreover, other systems, such as those disclosed in U.S. Pat. Nos. 3,958,573, 4,894,056, 3,863,641, 3,595,241, 396,754, 3,908,664 and 4,790,812 do not provide a closed sterile environment while still permitting easy clearing of drainage catheters.

OBJECTS OF THE INVENTION

One object of the invention is to provide device and method for sterilely removing occluded matter from wound drainage catheters.

Another object of the invention is to provide a closed wound drainage system in which drained matter can be stored in a reservoir for later analysis.

Another object of the invention is to provide a wound drainage system in which occluded material may be removed from a drainage catheter on multiple occasions.

BRIEF DESCRIPTION OF THE DRAWINGS

FIG. 1, shows a partial side section showing one embodiment of the invention.

FIG. 2 is a partial side section showing a multiple-plug version of the invention and a drainage catheter having saline lines.

FIG. 3 is a partial side section showing the sealed thread pulling mechanism of the present invention.

FIG. 4 is a partial side section showing how a replaceable handle may be used with the invention.

SUMMARY OF THE INVENTION

Figure 5:
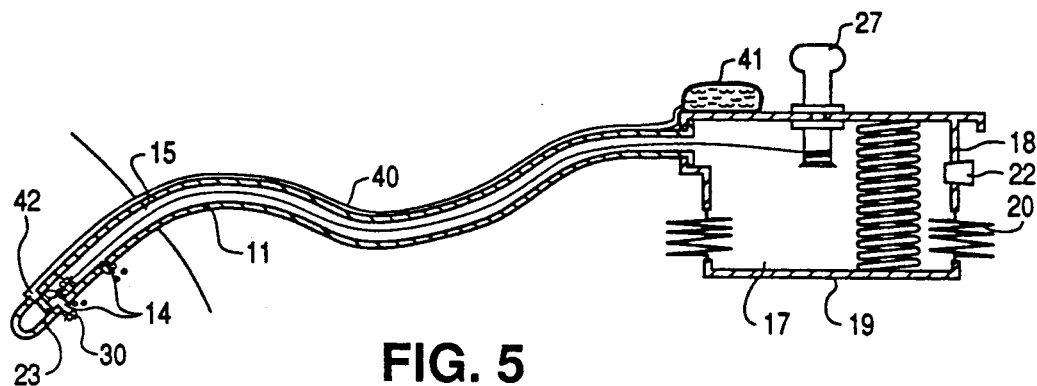
FIG. 5 is a view showing how saline solution may be introduced to the distal end of the lumen.

The invention consists of a wound drainage system having a wound drainage catheter with an apertured distal end and a closed reservoir system. A plug in the lumen of the distal end substantially engages the lumen. A thread connects the plug to a pulling mechanism external the closed reservoir system for pulling the thread to move the plug toward the suction end of the catheter to sterilely clear the lumen. The plug may have an aperture so that multiple plugs may be positioned in the lumen, with each plug thread passing through the aperture of each upstream plug. Each plug may be separately pulled through the lumen to clear catheter of occluded material.

DETAILED DESCRIPTION

Referring to FIG. 1, there is shown one embodiment of the present invention which includes catheter 11 in which distal end 13 is inserted into the wound site of patient 12. Distal end 13 contains a plurality of apertures 14 to allow fluid and other matter from within the patient to drain through catheter lumen 15. The suction end 16 of catheter 11 is sealably connected to closed reservoir system 17. Closed reservoir system 17 comprises a housing having upper 18 and lower 19 portions connected by an intermediate expandable bellows portion 20, such as a Snyder HEMOVAC compact evacuator available from Zimmer, Inc. of Dover Ohio Spring 21 also connects upper 17 and lower 19 reservoir portions. Upper portion 18 further includes reservoir plug 22 to provide access to the contents of reservoir 17. A vacuum pressure may be created in reservoir 17 by removing plug 22, compressing upper 17 and lower 19 portions together against the force of spring 21, and replacing plug 22. Spring 21 will bias upper 17 and lower 19 portions apart, thereby creating a vacuum in lumen 15.

Lumen plug 23 is positioned in the distal portion of lumen 15 beyond catheter apertures 14, and has a diameter to substantially engage the circumference of lumen 15. Vaseline may be placed on the periphery of plug 23 where it contacts lumen 15. Thread 24, which may be comprised of plastic, nylon, metal or the like, is connected to plug 23 and traverses the length of lumen 15 and is wrapped around spool 25. It will be understood by those of skill in the art that although the term "thread" is used to refer to the component connecting plug 23 to spool 25, any other suitable means for pulling plug 23 through lumen 15 may be employed, including without limitation metal cables or shafts, and such means are included within the meaning of the term "thread" herein.

As shown in FIGS. 3 and 4, spool 25 includes upwardly extending shaft 26 which passes through an aperture in upper housing 18. Handle 27 is threaded onto shaft 26 to permit manual rotation of spool 25 from the exterior of reservoir 17.

Figure 6:
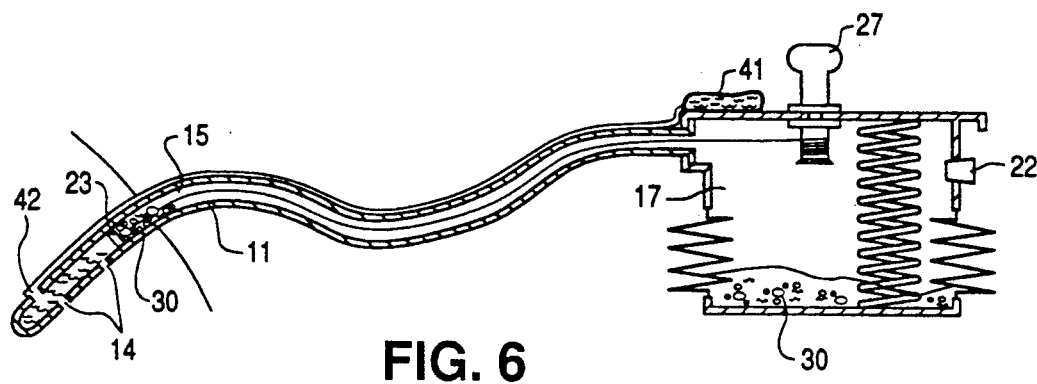
FIG. 6 is a view showing a partially depleted saline solution bag and a partially removed plug.
Figure 7:
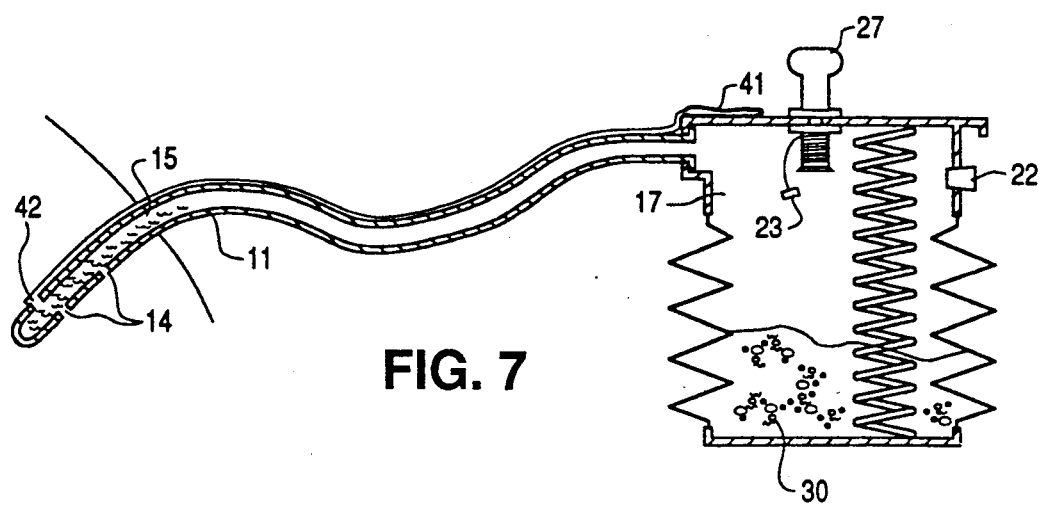
FIG. 7 is a view showing a fully removed plug in the reservoir and a fully depleted saline solution bag.

Referring now to FIG. 5, it is shown that fluid and particulate material 30 may enter catheter apertures 14 into lumen 15. At this point, plug 23 is positioned at the very tip of distal end 13, and it will be noted that collection reservoir 17 is empty. Fluid and other particulate material 30 may flow through lumen 15 as shown in FIG. 6 and be collected in reservoir 17. However, over time, lumen 15 may become occluded by particulate matter 30. In this event, handle 27, which is external to the closed reservoir, may be rotated to retract plug 23 past apertures 14, and eventually into reservoir 17 as shown in FIG. 7. It will be appreciated by those of skill in the art that passing plug 23 through the entire length of lumen 15 will sterilely scrape and clear the interior of lumen 15. Moreover, it will be appreciated that with the present invention this process may be accomplished without ever having to expose lumen 15 or collection reservoir 17 to a non-sterile environment.

FIGS. 5, 6 and 7 further demonstrate that it is possible to employ a catheter having an additional passageway 40 for the introduction to the wound site of saline solution which is kept in saline bag 41. In this embodiment, saline solution is introduced to distal end 13 of catheter 11 through saline aperture 42 after the plug 23 has been retracted. Moreover, as shown in FIGS. 6 and 7, as plug 23 is retracted through lumen 11, saline solution will be drawn into lumen 15 through saline apertures 42. This will assist drainage from the wound, help prevent catheter 11 from becoming occluded again, and will also maintain the same constant low suction within lumen 15 while the occluding clots and debris are being removed.

Figure 8:
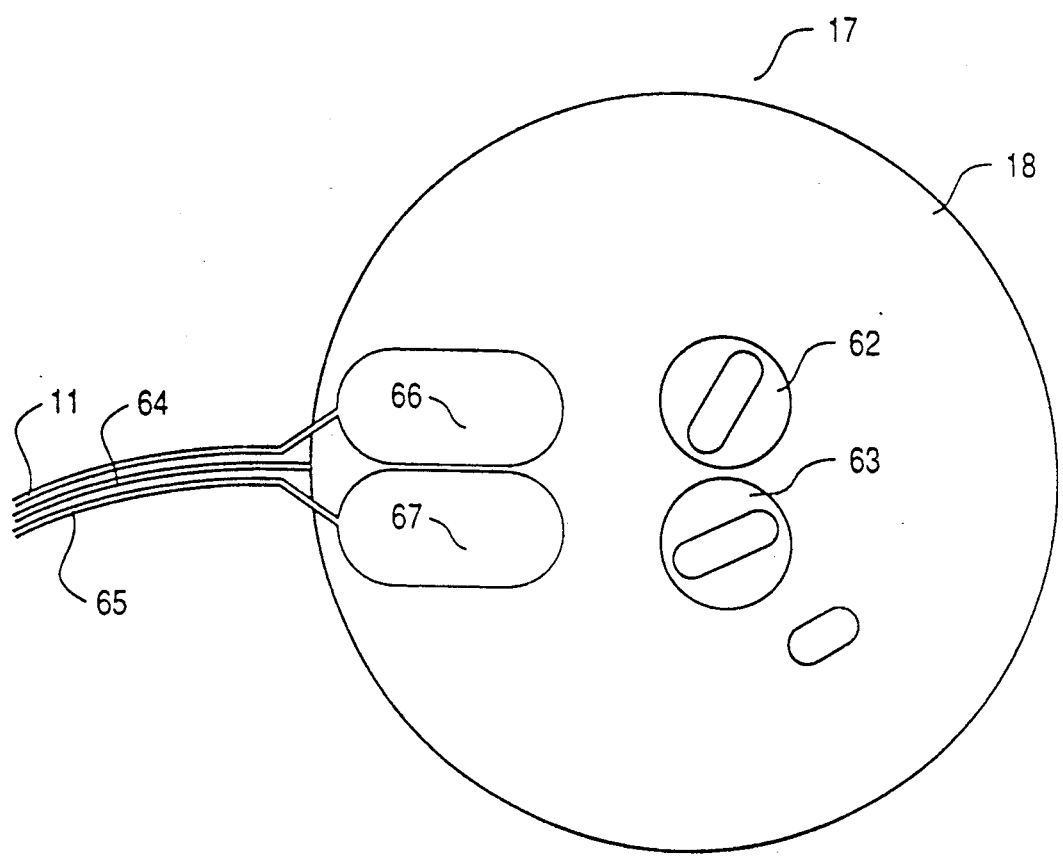
FIG. 8 is a top view showing an embodiment of the invention having two saline solution bags and two spool handles.

Referring now to FIG. 2, there is shown another embodiment of the invention showing how multiple plugs 51, 52 and 53 may be positioned at the distal end of catheter 11. This embodiment is particularly suitable for large surgical procedures such as radical mastectomies, abdominal perineal resections, and radical groin dissections. In this embodiment, plugs 51, 52 and 53 are all apertured and there is a separate thread for each plug. First thread 54 passes through apertures in both second 52 and third 53 plugs, while second thread 55 passes through an aperture in third plug 53. In this embodiment, the opposite ends of each thread may be connected to a separate spool-handle assembly. In addition, plugs 51, 52 and 53 are initially positioned over saline apertures 71, 72 and 73. This arrangement prevents saline solution from being drawn into reservoir 17 until one of the plugs is retracted. Thus, third plug 53 may be first retracted into reservoir chamber 17 to clear lumen 15 and simultaneously expose aperture 73 to permit saline to fill lumen 15. This retraction of plug 53 will not necessitate that plugs 51 or 52 be moved. Thereafter, if catheter 11 again becomes occluded, plug 52 may be retracted through lumen 11 to again clear it of occluded material, and permit saline solution from a second saline line to enter lumen 15 through aperture 52. Later, the same procedure may be repeated for first plug 51. Although three plugs are shown in FIG. 2, there is no theoretical limit to the number of plugs which may be so positioned in catheter 11. It will further be appreciated that when plugs 51, 52 and 53 are all in distal end 13 of catheter 11, the apertures in the plugs will permit material to enter catheter 11 and drain through plugs 51, 52 and 53 and into reservoir 17. It will also be appreciated that in the preferred embodiment, there will be a separate saline line for each plug, as shown in FIG. 8. This way, not all saline solution bags will be emptied when the first plug is retracted, but each plug will allow a fresh unit of saline to be drawn through lumen 15 and into reservoir 17. It will further be appreciated that the use of saline solution serves to prevent excessive vacuum pressure to act upon wound drainage apertures 14, as such excess pressure could cause fluid, tissue or debris to be pulled back through the plug. The saline solution permits a constant low suction to be maintained at wound suction apertures 14.

Referring to FIG. 8, there is shown a representative top-view of reservoir chamber 17 for a system having two catheter plugs. In this embodiment, there are two handles 62, 63, which may be connected to respective spools (not shown) on which threads 64 and 65 are wound. It is also possible to provide a catheter 11 having multiple passageways for communication of saline solution from saline bags 66, 67 to the distal end of the catheter.

It will be appreciated to those of skill in the art that many changes in the above-described embodiments could be made without departing from the spirit and scope of the invention. For example, other mechanisms for withdrawing the plug from the catheter while maintaining a closed system may be employed. For example, a motor driven spool could be positioned inside the reservoir which is actuated by a switch external to the reservoir, instead place of the manually rotated the spool. The present invention is also suitable for use with other types of reservoirs in addition to a spring suction reservoir, such as a balloon actuated evacuator, a bulb evacuator (available from Davol), or a catheter having a sufficiently sized suction end to permit removed material to be stored therein. It is also contemplated that any other suitable vacuum source may be introduced to the reservoir and/or catheter, this could be done for example, through plug 22 as shown in FIG. 1.

It will be appreciated that the present invention provides a device and method for cleaning wound drainage catheters from occlusions without breaching the sterile environment of the drainage system. Moreover, the present invention allows the wound drainage catheter to be cleaned on multiple occasions.

I claim:

1. A wound drainage system comprising:
   a wound drainage catheter having a lumen, an apertured distal end such that material to be drained may enter the lumen therethrough and a suction end,
   a closed reservoir system,
   the suction end of the catheter being sealably connected to the closed reservoir system such that material may drain from the distal end of the catheter into the closed reservoir,
   a plug in the lumen of the distal end of the catheter, the plug having a diameter to substantially engage the circumference of the lumen,
   a thread having one end connected to the plug, and
   pulling means external the closed reservoir system for pulling the thread to move the plug toward the suction end of the catheter to sterilely clear the lumen.

2. The wound drainage system of claim 1 wherein the plug has an aperture.

3. The wound drainage system of claim 2 further comprising
   at least one additional plug in the lumen of the distal end of the catheter,
   an additional thread for each additional plug, each additional thread having one end connected to its respective plug, each thread passing through an aperture of all plugs closer to the suction end that the respective plug.

4. The wound drainage system of claim 1 wherein the pulling means comprises a handle, a spool around which the thread is wrapped the spool having a shaft passing through the closed reservoir system such that the spool may be rotated by rotating the handle.

5. The wound drainage system of claim 1 further comprising means for introducing a liquid into the distal end of the lumen.

6. The wound drainage system of claim 5 wherein the liquid introducing means comprises an aperture in the distal end of the lumen, and wherein the plug is positioned in the lumen to cover such lumen aperture.

7. The wound drainage system of claim 1 wherein the reservoir comprises a spring suction reservoir.

8. The wound drainage system of claim 1 wherein the reservoir is expandable.

9. The wound drainage system of claim 1 further comprising a vacuum source applied to the catheter.

10. The wound drainage system of claim 1 wherein the thread comprises a metal cable.

11. The wound drainage system of claim 1 wherein the suction end of the catheter is sealably connected to the closed reservoir system.

12. The wound drainage system of claim 1 wherein the threads comprise metal cables.

13. A wound drainage system comprising:
   a wound drainage catheter having a lumen, an apertured distal end such that material to be drained may enter the lumen therethrough and a second end,
   first and second plugs in the lumen of the distal end of the catheter, the first plug having an aperture therethrough, each plug having a thread attached thereto,
   the thread attached to the second plug passing through an aperture of the first plug,
   such that the first plug may be pulled toward the suction end of the lumen to clear the lumen without causing the second plug to move, and such that the second plug may be later pulled toward the suction end of the lumen to clear the lumen.

14. The wound drainage system of claim 13 further comprising a closed reservoir system such that material may drain from the distal end of the catheter into the closed reservoir.

15. The wound drainage system of claim 13 further comprising means for applying a vacuum to the suction end of the catheter.

16. The wound drainage system of claim 13 wherein the first and second plugs have diameters that substantially engage the circumference of the lumen.

17. The wound drainage system of claim 13 further comprising
   pulling means external the closed reservoir system for pulling the threads to move the plugs toward the suction end of the catheter to sterilely clear the lumen.

18. The wound drainage system of claim 17 further wherein the pulling means comprise first and second handles, each handle, having a spool around which the thread is wrapped, the spool having a shaft passing through the closed reservoir system such that the spool may be rotated by rotating the handle.

19. The wound drainage system of claim 13 further comprising means for introducing a liquid into the distal end of the lumen.

20. The wound drainage system of claim 19 wherein the liquid introducing means comprises an aperture in the distal end of the lumen, and wherein at least one of the plugs is positioned in the lumen to cover such lumen aperture.

21. A method for sterilely clearing a wound drainage catheter, the catheter having an apertured distal end, a lumen and a vacuum end comprising:

providing a first plug in the lumen of the distal end of the catheter, the first plug having a diameter to substantially engage the circumference of the lumen, the first plug having a first thread attached thereto traveling through the lumen, placing the vacuum end of the catheter in communication with a closed reservoir, sterilely pulling the first thread to thereby move the first plug toward the suction end of the catheter without breaching the closed reservoir.

22. The method of claim 21 further comprising the step of sterilely applying a vacuum source to the vacuum end of the catheter.

23. The method of claim 21 wherein the providing step includes providing said plug with an aperture.

24. The method of claim 21 further comprising the steps of:

providing a second plug in the lumen of the distal end of the catheter, the second plug having a second thread attached thereto traveling through the lumen, the thread of the first plug passing through an aperture of the plug, and sterilely pulling the second thread to thereby move the second plug toward the suction end of the catheter without breaching the closed reservoir.

25. The method of claim 21 further comprising the step of introducing a liquid into the distal end of the lumen.

* * * * *